United States Patent [19]

Pinnavaia et al.

[11] Patent Number: 5,099,054
[45] Date of Patent: Mar. 24, 1992

[54] ORGANOCLAY TRIPHASE CATALYSTS

[75] Inventors: Thomas J. Pinnavaia; Chi-Li Lin, both of East Lansing, Mich.

[73] Assignee: Michigan State University, East Lansing, Mich.

[21] Appl. No.: 656,129

[22] Filed: Feb. 14, 1991

Related U.S. Application Data

[63] Continuation-in-part of Ser. No. 214,640, Jul. 1, 1988, abandoned.

[51] Int. Cl.$^5$ ............. C07C 29/143; C07C 41/16; C07C 45/29; B01J 31/00
[52] U.S. Cl. ..................... 558/10; 502/164; 558/344; 558/378; 568/59; 568/437; 568/630; 568/814; 585/436
[58] Field of Search ........... 568/59, 437, 630, 814; 558/10, 344, 378; 585/436

[56] References Cited

PUBLICATIONS

E. V. Dehmlow and S. S. Dehmlow, "Phase Transfer Catalysis", Verlag Chemie, Basel, (1983), pp. 1-3, 65-68, 371.
P. Monsef-Mirzai and W. R. McWhinnie, Inorg. Chim. Acta, vol. 52, (1981), pp. 211-214.
S. L. Regen, J. Amer. Chem. Soc., vol. 98, (1976), pp. 6270 to 6274.
S. L. Regen, J. Amer. Chem. Soc., vol. 97, (1975), pp. 5956-5957.
S. L. Regen, J. Org. Chem., vol. 42, (1977), pp. 875-879.
M. Schneider et al., J. Org. Chem., vol. 47, (1982), pp. 364-365.
P. Tundo et al., J. Amer. Chem. Soc., vol. 104, pp. 6547 to 6551 and pp. 6551 to 6555, (1982).
Kadkhodayan and Pinnavaia, "Journal of Molecular Catalysis", vol. 21, pp. 109-117 (1983).
Cornelis and Laszlo, "Synthesis", pp. 162-163 (Feb. 1982).

*Primary Examiner*—J. E. Evans
*Attorney, Agent, or Firm*—Klauber & Jackson

[57] ABSTRACT

In a method of carrying out organic conversions via heterogeneous phase transfer catalysis by contacting immiscible liquid phases containing respective substances capable of interacting, with a solid catalyst to promote the transfer of reactive species from one liquid phase to another, the improvement comprises employing as catalyst a cation exchanged form of a 2:1 layered silicate clay with layer charge densities in the range of above 0.4 to 2.0 containing an onium ion containing one or more alkyl hydrocarbon chains and maintaining the materials in emulsified form by having a sufficient chain length of an alkyl group relative to the charge density of the clay.

10 Claims, 1 Drawing Sheet

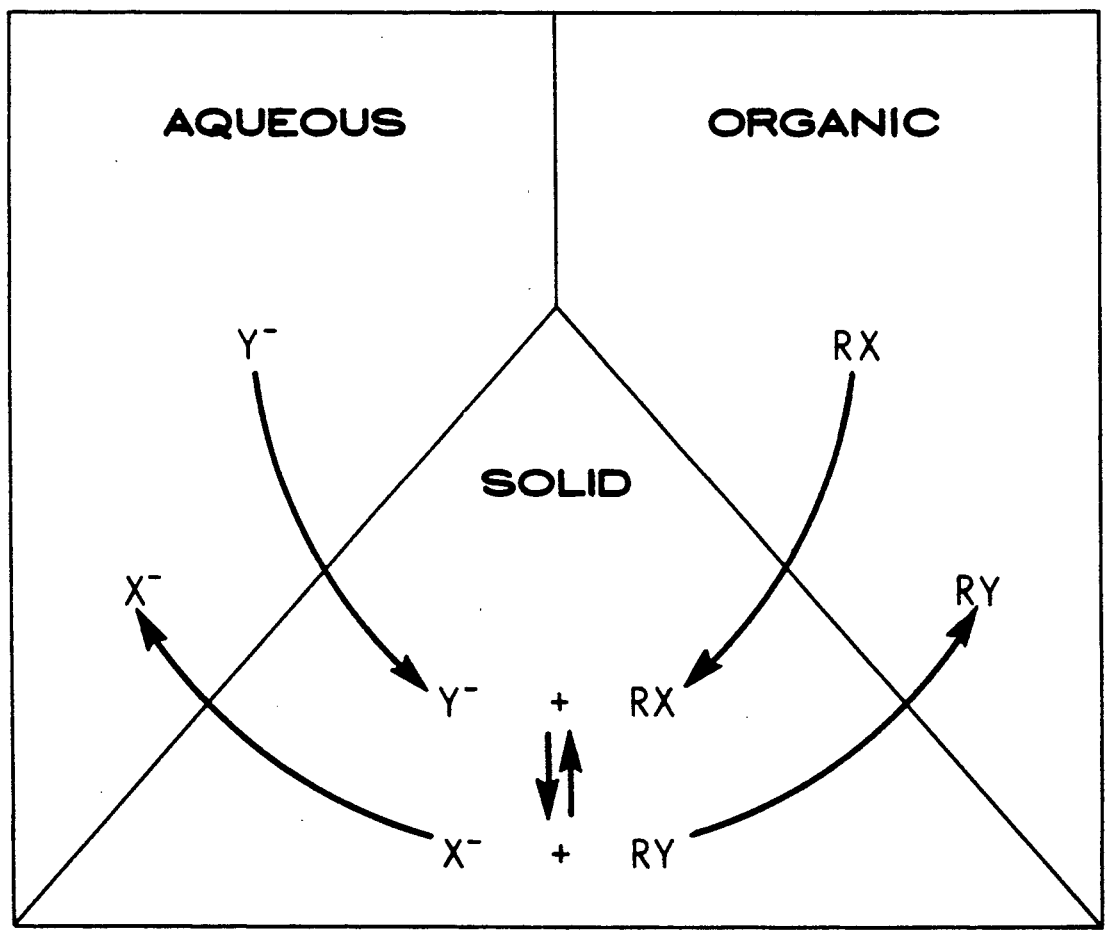

ORGANOCLAY TRIPHASE CATALYSTS

This application is a continuation-in-part of application Ser. No. 214,640, filed Jul. 1, 1988, now abandoned.

FIELD OF THE INVENTION

This invention relates to heterogeneous phase transfer catalysis, based upon the emulsion-stabilizing properties of onium ion smectite clays and e.g., triphase catalysis, useful for organic nucleophilic substitution conversions in which the function of the heterogeneous or solid phase catalyst is to bring the reagents together in emulsified form to form the products in the interfacial region between the solid catalyst and the immiscible liquid phases bearing the reagents.

In a typical triphase catalyst system, reagents from two immiscible liquid phases, usually an aqueous phase and an organic phase, are transferred to the interface of a solid phase where they undergo reaction. The simplicity of catalyst recovery is generally recognized as an important practical advantage of triphase catalysis over conventional liquid-liquid phase transfer catalysis.

BACKGROUND OF THE INVENTION

In effecting organic chemical conversions, particularly nucleophilic substitution reactions, one frequently encounters the problem of bringing together reagents in sufficient concentration to attain conveniently rapid reaction rates. The classical solution to this problem is simply to use a polar aprotic solvent (e.g., acetonitrile, acetone, dichloromethane, dioxane) which can dissolve both reagents, e.g., a mutual solvent. However, the use of a single solvent is not always feasible, particularly on an industrial scale. Such solvents frequently are expensive, difficult to remove after the reaction; and may present environmental problems. The technique of phase transfer catalysis, see E. V. Dehmlow and S. S. Dehmlow, "Phase Transfer Catalysis", Verlag Chemie, Basel, (1983), pp. 1-3, 65-68, 371, provides a method which avoids the use of polar aprotic solvents and allows reactions to be carried out in mixtures of immiscible liquid phases. An article cited by Dehmlow, by P. Monsef-Mirzai and W. R. McWhinnie, Inorg. Chim. Acta, vol. 52, 211 (1981) is of general interest.

In the phase transfer technique the polar reagents are dissolved in a polar solvent, (most typically, water) and the nonpolar or organophilic reagents are used as neat liquids or are dissolved in a suitable organic solvent (e.g., toluene, xylene, diesel oil). A catalyst, typically an onium ion, particularly an alkyl-ammonium or phosphonium ion, is then added which transfers reagents from the immiscible polar phase to the organic phase where reaction occurs. The catalyst then is transferred back to the polar liquid phase by the polar reaction products and the cycle is continuously repeated. Micelles can also be formed which allow the polar reagent and organic reagent to come together in the aqueous phase.

One serious disadvantage of soluble phase transfer catalysts is that they are expensive and must be removed from the reaction mixture at some later stage. Distilling the solvents to recover the catalysts is time and energy consuming. Also, soluble phase transfer catalysts sometimes cause undesirable foaming of the reaction mixture and do not lend themselves to convenient chemical processing methods.

Heterogeneous phase transfer catalysis, sometimes called triphase catalysis, has been developed to solve these problems, see S. L. Regen, J. Amer. Chem. Soc., vol. 98, 6270 (1976). From the viewpoint of industrial applications, heterogeneous phase transfer catalysts are very attractive because they are easily recovered by filtration and because they are ideally suited for continuous flow processing methods. The heterogeneous phase transfer catalysts developed to date make use of polymers (e.g., polystyrene) see S. L. Regen, J. Amer. Chem. Soc., vol 97, 5956 (1975) and J. Org. Chem., vol. 42, 875 (1977), also M. Schneider et al, J. Org. Chem., vol. 47, 364 (1982), or metal oxides (e.g., silica, alumina) see P. Tundo et al, J. Amer. Chem. Soc., vol. 104, pp. 6547 and 6551 (1982). These solids have been functionalized so that polar reagents, particularly anions, can bind electrostatically to their surfaces. Also, their surfaces are sufficiently organophilic so that organic reagents will adsorb on their surfaces and undergo reaction with the immobilized polar reagent.

Polymer-based heterogeneous phase transfer reagents are sometimes limited by diffusion of reagents into and out of the polymer matrix. Also, swelling of the polymer matrix by the reagents or products can make it difficult to regulate the diffusion process. Even under the best of technical conditions, polymer-based catalysts suffer the economic disadvantage of high manufacturing costs. Oxide-based phase transfer catalysts also are expensive to manufacture. To functionalize oxide surfaces with appropriate alkylammonium or alkylphosphonium ions, one must covalently link the ions to the surface through the use of a coupling agent, usually a silane. These functionalized oxides often are not easily dispersed in the reaction mixture and reaction rates are often limited by relatively low surface areas.

In formulating a heterogeneous phase transfer reagent, one needs to optimize the surface area of the interfacial region between the solid catalyst and the immiscible liquid phases, because it is this interface which is important in bringing together the reacting reagents. FIG. 1 illustrates this concept. $Y^-$ represents the water soluble polar reagent or reactive species and RX is the organophilic reagent contained in the immiscible organic phase. The function of the heterogeneous or solid phase is to bring the reagents together to form RY and $X^-$ as products in the interfacial region between the solid catalyst and the liquid phases.

Kadkhodayan and Pinnavaia in Journal of Molecular Catalysis, vol. 21, pp. 109-117 (1983) have previously demonstrated that intercalated smectite clays were useful heterogeneous phase transfer reagents. In these systems the interlayer regions were occupied by layers of organometallic cations and inorganic anions. One severe limitation, however, was that the intercalated salt was eventually desorbed from the clay interlayers and lost to solution, the advantages of a solid state phase transfer catalyst thereby being lost. Cornelis and Laszlo in Synthesis, pp. 162-163 (February 1982) used a commercially available organocation clay (Tixogel) as a phase transfer catalyst for a specific type of organic conversion.

In general, the present invention concerns a method in which organoclays, e.g., cation exchanged forms of swelling 2:1 layered silicate clays containing alkylammonium, alkylphosphonium or related "onium" ions, provide efficient interfacial surfaces for the catalysis of organic conversions in which the reagents and products are partitioned between two or more immiscible liquid phases.

SUMMARY OF THE INVENTION

It has now been found that, in a method of carrying out an organic chemical conversion particularly a nucleophilic substitution reaction at the electrophilic center of an organic substrate by heterogeneous phase transfer catalysis wherein the immiscible liquids respectively containing reactive species, are brought into contact by emulsion formation with an onium ion exchange form of a smectite clay so that reaction occurs, an improvement is obtained via employing as catalyst a cation exchanged form of a 2:1 layered silicate clay, e.g., a smectite-type clay containing an onium cation containing one or more alkyl hydrocarbon chains and maintaining the materials in emulsified form by having a sufficient chain length of an alkyl group relative to the charge density of the clay. Essentially, an onium cation is required containing a hydrocarbon chain sufficiently long in relation to layer charge to cause emulsion formation.

Any onium cation containing one hydrocarbon chain and maintaining the materials in emulsified form is sufficient. However, quaternary onium ions of the type $R_4A^+$, wherein A=N, P, or As and R represents an organo group, are preferred. The four R groups may be of the same type, or they may differ. Primary, secondary, and tertiary onium ions of the type $RAH_3^+$, $R_2AH_2^+$, $R_3AH^+$, respectively, can decompose on the clay surfaces, and there can be loss of the organic fraction by volatilization of the uncharged (neutral) conjugate base. For instance, in the case of a primary ammonium ion on a clay surface, reaction with water or other bases (B) can occur to liberate the free amine:

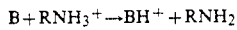

$$B + RNH_3^+ \rightarrow BH^+ + RNH_2$$

Quaternary onium ions of the type $R_4A^+$ (A=N, P, or AS) do not react like this and will not be lost.

The preferred compositions of the quaternary onium ions can be represented in general form by the formula $[R_{4-x}AR'_x]^+$ where R is a large organo group consisting of a straight- or branched-chain alkyl group typically containing six or more carbon atoms and R' is a small organo group typically containing four or less carbon atoms (e.g., methyl, ethyl, propyl, butyl, ethoxyl, or propoxyl), a phenyl group ($-C_6H_5$), a benzyl group ($-CH_2C_6H_5$) or a combination of such groups. When all four organo groups are identical, x=0. The R' groups may contain fewer than six carbon atoms, depending on the charge density of the clay (see below).

In another embodiment, the clay-bound onium ion can be an N-alkylonium salt of a teteroarene such as an alkylpyridinium ion of the type $[C_5H_5NR]^+$ where R is a large organo group consisting of a straight- or branch-chain alkyl group containing typically five or more carbon atoms. Smectite clays exchanged with onium ions with chiral centers, such as (1R,2S) (-)-N-dodecyl-N-methylephedrium, are particularly useful for catalyzing dissymmetric nucleophilic substitution reactions. Smectites exchanged with chiral (8R,9S) (-)-benzylquinium ions also are useful as catalysts for dissymmetric organic conversions.

The examples below illustrate the use of organoclays in catalyzing a general class of reactions in which one reagent is dissolved in water and the second reagent is dissolved in or is itself an immiscible organic medium. The reagent which is dissolved in water normally is not soluble in an organic solvent. When the organic reagent is a liquid, it may function as its own solvent, immiscible with water. If the organic reagent is a solid, an organic solvent is needed to bring it into solution. However, if the organic reagent is itself a liquid, then no organic solvent may be necessary.

Nucleophilic substitution reactions are the most important class of reactions that may be catalyzed by organoclays. However, other types of reactions, such as electron transfer or oxidation-reduction reactions, may also be catalyzed thereby.

The term "nucleophilic" may be defined as having an attraction for positive charges, as opposed to "electrophilic" which may be defined as having an attraction for electrons. For example, in the reactions contemplated, one reactant A soluble in a polar or aqueous solvent may be nucleophilic, i.e., negatively charged or electron rich, whereas the other reactant B soluble in an organic solvent may be electrophilic, i.e., electron deficient. The reaction may be viewed as a nucleophilic attack by reactant A on reactant B. In regard to mechanism, one may visualize that the organoclay may engulf a packet of the organic phase, encapsulating it, and bring it into the aqueous phase. The system is a clay stabilized or clay mediated emulsion. The clay mixes the two phases and probably facilitates transfer of reagents between them. In any event, the solid organoclay phase functions to provide good contact between the reagents by providing an interfacial region of high surface area between the solid and the immiscible liquid phases, in which interfacial region the reagents are brought together to form the products.

The term "reactive species" may be used herein to designate a constituent of a reactive substance or reagent, such as an ion.

For an organoclay to function as an emulsion former and a high reactivity phase transfer catalyst, a certain relationship between the size of the large organo groups and the charge density on the clay must be realized. It is believed that the quaternary onium ion should have present a hydrocarbon chain which orients on the surface so that the large organo group extends away from the surface rather than being aligned with the surface; and that this alignment of chains enables the clay to stabilize droplets of the organic solvent or liquid reagent in aqueous solution. For smectite clays with charge density typically in the range of 0.6 to 1.2 charge units per $O_{20}(OH)_4$ unit, the quaternary onium ion should contain at least one chain with five carbon atoms, and the other three alkyl groups may have smaller carbon chains including single-carbon methyl groups. For low charge density clays, the hydrocarbon chain lengths necessary to orient the chain in the desired conformation may be substantially larger than five carbon atoms. For instance, the synthetic smectite clay known as Laponite with a charge density of only 0.4 electrons per $O_{20}(OH)_4$ unit is not a substantially active phase transfer catalyst even when hexadecyltrimethylammonium ions are exchanged on the basal surfaces of the clay. On the other hand, a very high charge density clay, such as fluorohectorite with a charge density of 1.5 charge units per $O_{20}(OH)_4$ unit, intercalates the organo chains in the desired orientation. In short, the size of the onium ion hydrocarbon chain needed for efficient organoclay phase transfer catalysts depends on the charge density of the clay. In general, the higher the charge density of the smectite clay, the smaller the size of the large organo group needed. Very high charge density clays such as vermiculite or synthetic 2:1 layered silicates with cation exchange properties, including synthetic mica-montmorillonite, tetrasilicic mica or fluorohectorite, (1.5–2.0 charge units per $O_{20}(OH)_4$, $O_{20}(OH,F)_4$ or $O_{20}F_4$ unit) may form emulsions with quaternary onium ions as small as trimethyl ammonium ions and trimethylbutyl ammonium. In the preferred embodiment of this invention the size of the large organo group is geared to the charge density of the clay.

The article by Cornelis and Laszlo referred to above made use of a clay surface as a carrier of alkylammonium ion for transfer to the organic phase where ion pairs were formed in accord with the teachings of conventional phase transfer catalysis. The identity of the organo cation on the clay used in their experiments is not provided. The present system differs fundamentally from the general knowledge available in the art. The organoclays used herein represent a specific family of 2:1 layered silicate materials that are unusually efficient in forming a triphase emulsion useful for catalyzing phase transfer reactions. The clay support in our invention is not used merely as a carrier for an onium ion catalyst. Instead, our invention is based on specific combinations of onium ions and smectite clays that are capable of forming stable emulsions; the emulsions themselves are the active catalyst medium. The emulsion forming property allows the reagents to be brought together in an efficient manner. An organoclay which does not form an emulsion exhibits inferior catalytic reactivity. Thus, the present invention teaches this principle and makes a distinction between organoclays capable of functioning as emulsion formers, and those which are not. The Cornelis and Laszlo article gives no indication of these teachings.

BRIEF DESCRIPTION OF THE DRAWING

The single FIGURE is a schematic illustration of triphase catalysis system such as may be carried out according to the invention in connection with the use of an organoclay.

DETAILED DESCRIPTION

Synthesis of Organoclay Phase Transfer Catalysts

An aqueous suspension of a smectite clay was stirred vigorously for 24 hours with a known amount of an alkylammonium or alkylphosphonium salt dissolved in water or methanol solution. The products were washed free of excess onium salt with methanol, re-suspended in water, collected by centrifugation, and air dried at room temperature. Table 1 provides examples of products obtained by reaction of 0.5 wt % Na+-hectorite in water with various amounts of $C_{16}H_{33}NMe_3^+$ (Me=methyl) dissolved either in water (samples 1AA–7AA) or in methanol (samples 1AM–7AM). Analogous products obtained by reaction of the aqueous clay suspension with $Bu_4N^+$ (Bu=n-butyl) in water and methanol are identified as samples 8AA–14AA and 8AM–14AM, respectively. For both types of reaction conditions, the displacement of Na+ exchange ions by onium ions was very strongly favored. Nearly complete exchange was achieved using stoichiometric amounts of reagents. The use of a 2 to 10 fold excess of onium ion assured complete exchange and formation of a homoionic product. Products prepared using less than a stoichiometric amount of onium ions represent mixed (Na+ and onium ion) exchange forms of the clay. Optimum $d_{001}$ spacings were obtained for the $C_{16}H_{33}NMe_3^+$ exchange forms when the number of onium ion equivalents used in the reaction was comparable to the cation equivalents of clay (~73 meq/100 g). The $Bu_4N^+$-hectorite products gave $d_{001}$ values independent of onium ion loading.

Test of Catalytic Activity

Catalytic activity under triphase conditions was established by determining the pseudo first-order rate constant ($k_{obs}$) for the reaction of an alkylbromide in organic solvent (e.g., toluene) with KCN in aqueous solution to yield a nitrile. In a typical experiment the air-dried organoclay (either 0.1 g or 0.073 meq, depending on the experiment) was dispersed in 3.0 ml of 6.67 M aqueous KCN in a 15×150 mm Pyrex culture tube fitted with a Teflon-lined screw cap. The mixture was stirred vigorously with a magnetic stirring bar for 3–4 hours and then 6 ml of toluene or other organic solvent was added along with 2.0 mmole of alkylbromide. The tube was then immersed in an oil bath at 90.0°±0.5° C. while vigorous stirring was maintained. Reaction rates were determined first centrifuging, and then withdrawing 1 ul samples from the upper organic layer and analyzing the products mixtures by GC (gas chromatography) (HewlettPackard Model 5880A chromatograph with flame ionization detector and capillary column, 12.5 m×0.2 nm, and containing cross-linked dimethylsilicone). The reproducibility for the observed (obs.) rate constants typically was within 5%. A similar method was utilized in studying the reaction rate under biphase reaction conditions, wherein an equivalent amount of onium salt was used in place of the organoclay catalyst. The values $k_{obs}$ for the triphase organoclay systems were compared with the corresponding $k_{obs}$ values for the equivalent clay-free biphase catalyst system.

Summary of Catalytic Properties

Table 1

The data in Table 1 show that organic onium ion exchange forms of hectorite, a typical swelling 2:1 layered silicate clay, were catalysts for the conversion of $C_5H_{11}Br$ to $C_5H_{11}CN$ under triphase reaction conditions. Even partially exchanged products containing both Na+ and onium ions (e.g., Samples 1AA–3AA and 1AM–3AM) gave $k_{obs}$ values substantially larger than those obtained with no catalyst (cf., Blank 1) or with homoionic Na+-hectorite as catalyst (cf., Blank 2). The optimum reaction rates were obtained with the homoionic exchange forms of the clay (cf., samples 4AA–7AA, 4AM–7AM, 11AA–14AA, and 11AM–14AM). Thus, swelling clays having as few as about 25% of the inorganic exchange ions replaced by organic onium ions were catalytically active, but homoionic derivatives in which all of the exchange ions were organic onium ions were preferred.

The hectorite clays containing $[C_{16}H_{33}NMe_3]^+$ ions gave catalytic reaction mixtures for $C_5H_{11}Br$ to $C_5H_{11}CN$ conversions which were uniform organic liquid-water-clay colloid emulsions. The emulsions were easily broken by low speed centrifugation. Hectorites containing $[Bu_4N]^+$ were less active than those containing $[C_{16}H_{33}NMe_3]^+$. The former clays formed triphase reaction mixtures in which the organic liquid, water, and clay spontaneously separated into separate phases upon cessation of stirring. These results, along with those discussed further below, demonstrated that organoclays which formed emulsions under triphase reaction conditions were more active catalysts than those which did not. Thus, organoclays which formed emulsions were the candidate of choice. The emulsions are relatively stable and they take a long time to break on their own. However, they are very easily broken by centrifugation or by filtering.

All three phases enter into emulsion formation (organic phase + water phase + clay phase). Under typical reaction conditions, the emulsions are of the oil-in-water type, except that the clay phase plays an essential role in stabilizing the emulsion, and making it more effective than the mixture which would be formed in the absence of organoclay. More water can be added to the emulsion without the water separating from the emulsion. However, if more organic phase is added to the emulsion it will separate from the emulsion as a separate liquid phase. This is the evidence that the emulsions are organoclay-stabilized liquid organic droplets dispersed in an aqueous phase. The emulsion is indeed a triphase system, consisting of two liquid phases and a solid phase.

It is significant that $[C_{16}H_{33}NMe_3]^+$ supported on swelling clay was about 2.25 times as active as the unsupported ion under comparable reaction conditions (cf., Table 2, samples 19AA and 19AM). In contrast, $Bu_4N^+$ supported on hectorite was only 0.125 times as active as the unsupported catalyst (cf., Samples 18AA and 18AM). Thus, the clay environment can substantially mediate the properties of onium ions as phase transfer catalysts.

Table 2

The data in Table 2 for $C_5H_{11}Br$ to $C_5H_{11}CN$ conversion show that a number of onium ions can be utilized in the synthesis of organoclay triphase catalysts. Included in the Table are the $k_{obs}$ values for the same onium ions under equivalent biphase reaction conditions in the absence of a solid phase (cf., values in parentheses). In most cases the $k_{obs}$ values under triphase conditions were lower than the $k_{obs}$ values under biphase reaction conditions. However, the convenience and efficiency of recovery of the organoclay catalyst more than compensated for the reduced activity.

For a given clay host the phase transfer catalyst activity of its onium ion derivatives is not correlated with $d_{001}$ spacing or with the intrinsic activity of the onium ion as a biphasic catalyst.

The catalytic activity of a series of onium ion exchange forms of hectorite was found to increase in the order $[Bu_4N]^+$ (sample 18AA and 18AM) < $[Me_2N(C_{12}H_{25})_2]^+$ (sample 24AA and 24AM) < $[MeN(C_8H_{17})_3]$ (sample 25AA and 25AM) < $[Bu_3PC_{16}H_{33}]^+$ (sample 26AA and 26AM). Aryl groups may also be present as in samples 21AA through 23AM.

All of the more active homoionic onium ion exchange forms of hectorite shown in Table 2 (samples 19AA through 26AM) formed uniform emulsions under triphase reaction conditions. The less active exchange forms (sample 15AA through 18AM) did not form emulsions. Thus onium ions which impart emulsion forming properties to swelling clays under triphase reaction conditions are preferred.

Tables 3 and 4

The data in Tables 3 and 4 illustrate that reaction rates under triphase conditions were linearly dependent on the organoclay concentration and KCN concentration. These results were consistent with the transfer of reagents to the interfacial region between the clay and the liquid phases.

Table 5

The results in Table 5 show that organohectorites were useful catalysts for the chemical conversion of other alkyl bromides to alkylcyanides. Increasing the alkyl bromide chain length to nine or twelve carbon atoms did not dramatically alter the reaction rate.

Table 6

This table illustrates the effect of clay layer charge on catalytic efficiency. Three clays of different layer charge densities were investigated: Laponite, a synthetic hectorite manufactured by Laporte Industries, Ltd., with a charge density of about 0.4 $e^-$ per $O_{20}(OH)_4$ unit; a natural hectorite (California) with a charge density of about 0.6 $e^-$ per $O_{20}(OH,F)_4$ unit; a synthetic fluorohectorite with about 1.8 e per $O_{20}F_4$ unit. The $k_{obs}$ values of the homoionic $[C_{16}H_{33}NMe_3]^+$ and $[Bu_4N]^+$ exchange forms for $C_5H_{11}Br$ to $C_5H_{11}CN$ conversion show that catalytic activity was lowest for Laponite. Increasing the charge density to that of hectorite and fluorhectorite resulted in increased activity. The low $d_{001}$ value for $[C_{16}H_{33}NMe_3]^+$-Laponite indicated that the onium ion is oriented with the hydrocarbon chain essentially parallel to the silicate surface. In $[C_{16}H_{33}NMe_3]^+$-hectorite, with $d_{001}=18.0$ A the chains are inclined with regard to the layers. The $[C_{16}H_{33}NMe]^+$ in F-hectorite forms a lipid-like bilayer, as indicated by the $d_{001}$ value of 28 A. These results indicate that for a given onium ion, a clay host with sufficient layer charge to cause inclination of the alkyl chains relative to the silicate layers, is preferred. The charge density needed to cause inclination of the onium ion chains will depend on the size of the onium ion, but a value near $0.6e^-$ per $O_{20}(OH,F)_4$ unit is typical.

The orientation of $[Bu_4N]^+$ ions in the interlayers of Laponite and hectorite was similar, as was indicated by the $d_{001}$ values of 14.0 and 14.7 A, respectively. Yet, the $k_{obs}$ value for hectorite was 4.35 times as large as the value for Laponite. Thus, higher clay charge densities which increase the density of onium ions in the interlayer and improve the organophilic character of the interlayer are preferred.

TABLE I

Organoclays Containing $[C_{16}H_{33}NMe_3]^+$ and $[Bu_4N]^+$ Exchange Ions

| Organoclay | Number | ml 0.5 Wt % Na-Hectorite in water | ml 0.073M Onium Ion in water | ml 0.073M Onium Ion in methanol | onium meq clay | $d_{001}$, A Air-dried Product | $k_{obs}{}^a$, $hr^{-1}$ |
|---|---|---|---|---|---|---|---|
| Blank 1[b] | — | — | — | — | — | — | 0.000 |
| Blank 2[c] | — | — | — | — | — | — | 0.001 |
| $[C_{16}H_{33}NMe_3]^+$- | 1AA | 200 | 2.5 | — | 0.25 | 14.0 | 0.009 |
| Hectorite (d) | 2AA | 200 | 5.0 | — | 0.50 | 15.0 | 0.040 |
|  | 3AA | 200 | 7.5 | — | 0.75 | 17.4 | 0.093 |
|  | 4AA | 200 | 10.0 | — | 1.00 | 17.7 | 0.130 |
|  | 5AA | 200 | 20.0 | — | 2.00 | 18.2 | 0.138 |
|  | 6AA | 200 | 30.0 | — | 3.00 | 18.0 | 0.126 |

TABLE I-continued

Organoclays Containing $[C_{16}H_{33}NMe_3]^+$ and $[Bu_4N]^+$ Exchange Ions

| Organoclay | Number | ml 0.5 Wt % Na-Hectorite in water | ml 0.073M Onium Ion in water | ml 0.073M Onium Ion in methanol | onium meq clay | $d_{001}$, Å Air-dried Product | $k_{obs}^a$, hr$^{-1}$ |
|---|---|---|---|---|---|---|---|
| | 7AA | 200 | 100 | — | 10.00 | — | 0.129 |
| $[C_{16}H_{33}NMe_3]^+$- | 1AM | 200 | — | 2.5 | 0.25 | 14.0 | 0.016 |
| | 2AM | 200 | — | 5.0 | 0.50 | 14.1 | 0.038 |
| | 3AM | 200 | — | 7.5 | 0.75 | 16.4 | 0.095 |
| | 4AM | 200 | — | 10.0 | 1.00 | 18.0 | 0.118 |
| | 5AM | 200 | — | 20.0 | 2.00 | 18.0 | 0.138 |
| | 6AM | 200 | — | 30.0 | 3.00 | 18.0 | 0.134 |
| | 7AM | 200 | — | 100 | 10.00 | 18.0 | 0.129 |
| $[Bu_4N]^+$-Hectorite | 8AA | 200 | 2.5 | — | 0.25 | 14.5 | |
| | 9AA | 200 | 5.0 | — | 0.50 | 14.7 | |
| | 10AA | 200 | 7.5 | — | 0.75 | 14.7 | |
| | 11AA | 200 | 10.0 | — | 1.00 | 15.1 | |
| | 12AA | 200 | 20.0 | — | 2.00 | 15.1 | |
| | 13AA | 200 | 30.0 | — | 3.00 | 14.7 | |
| | 14AA | 200 | 100 | — | 10.00 | 14.7 | |
| $[Bu_4N]^+$-Hectorite | 8AM | 200 | — | 2.5 | 0.25 | 14.7 | |
| | 9AM | 200 | — | 5.0 | 0.50 | 14.7 | |
| | 10AM | 200 | — | 7.5 | 0.75 | 14.7 | |
| | 11AM | 200 | — | 10.0 | 1.00 | 14.7 | |
| | 12AM | 200 | — | 20.0 | 2.00 | 14.7 | |
| | 13AM | 200 | — | 30.0 | 3.00 | 14.7 | |
| | 14AM | 200 | — | 100 | 10.00 | 14.7 | |

$^a$Pseudo first order rate constant for conversion at 90° C. of pentylbromide to the corresponding n The following amounts of reagents were used: 2.0 mmole $C_5H_{11}Br$ in 6.0 ml toluene; 20.0 mmole KCN in 3.0 ml water; 0.10 g organoclay.
$^b$No clay or onium was used in this blank run.
$^c$Na$^+$-hectorite was used as catalyst in this blank run.
$^d$$C_{16}H_{33}$ = n-hexadecyl

TABLE 2

Homoionic Organohectorites as Phase Transfer Catalysts

| Onium Ion$^d$ | Sample Number$^a$ | $d_{001}$, Å Air-dried | Triphase $k_{obs}$, hr$^{-1b}$ |
|---|---|---|---|
| $[C_6H_5CH_2NMe_3]^+$ | 15AA | 14.7 | 0.006 |
| | 15AM | 14.7 | 0.006 |
| | — | — | (0.005)$^c$ |
| $[C_6H_5CH_2P(C_6H_5)_3]^+$ | 16AA | 18.4 | 0.012 |
| | 16AM | 18.4 | 0.014 |
| | — | — | (0.005) |
| $[CH_3NC_5H_5-C_5H_5NCH_3]^{2+}$ | 17AA | 13.0 | 0.003 |
| | — | — | (0.000) |
| $[Bu_4N]^+$ | 18AA | 14.7 | 0.074 |
| | 18AM | 14.7 | 0.067 |
| | — | — | (0.563) |
| $[Me_3NC_{16}H_{33}]^+$ | 19AA | 18.0 | 0.164 |
| | 19AM | 18.0 | 0.161 |
| | — | — | (0.073) |
| $[Me_3NC_{14}H_{29}]^+$ | 20AA | 17.0 | 0.142 |
| | 20AM | 17.0 | 0.122 |
| | — | — | (0.066) |
| $[C_6H_5CH_2NMe_2C_{14}H_{29}]^+$ | 21AA | 18.1 | 0.163 |
| | 21AM | 18.0 | 0.153 |
| | — | — | (0.383) |
| $[C_6H_5CH_2NMe_2C_{16}H_{33}]^+$ | 22AA | 18.3 | 0.161 |
| | 22AM | 18.3 | 0.165 |
| | — | — | (0.369) |
| $[C_6H_5CH_2NMe_2C_{18}H_{37}]^+$ | 23AA | 18.3 | 0.164 |
| | 23AM | 18.4 | 0.162 |
| | — | — | (0.418) |
| $[Me_2N(C_{12}H_{25})_2]^+$ | 24AA | 20.1 | 0.162 |
| | 24AM | 20.5 | 0.165 |
| | — | — | (0.541) |
| $[MeN(C_8H_{17})_3]^+$ | 25AA | 21.0 | 0.181 |
| | 25AM | 20.1 | 0.185 |
| | — | — | (1.10) |
| $[Bu_3PC_{16}H_{33}]^+$ | 26AA | 20.1 | 0.846 |
| | 26AM | 20.5 | 0.860 |
| | — | — | (2.20) |

$^a$The description AA indicates the clay was synthesized by ion exchange of Na$^+$-hectorite in aqueous medium. The designation AM indicates the organoclay was prepared in aqueous methanol. In both types of synthesis 2 meq of onium ion was used per meq of clay.
$^b$The triphase $k_{obs}$ values are for the conversion of $C_5H_{11}Br$ to $C_5H_{11}CN$ at 90° C. under the following conditions: 2.0 mmole $C_5H_{11}Br$ in 6.0 ml toluene, 20 mmole KCN in 3 ml water, 0.073 meq. organoclay.
$^c$Values in parenthesis are $k_{obs}$ values determined under equivalent biphase conditions, wherein an equivalent amount of onium ion was present as a soluble Br$^-$ or Cl$^-$ salt.
$^d$In the formulas shown $C_{16}H_{33}$ = n-hexadecyl; $C_{14}H_{29}$ = n-tetradecyl; $C_{18}H_{37}$ = n-octadecyl; $C_{12}H_{25}$ = n-dodecyl; $C_8H_{17}$ = n-octyl; $C_6H_5CH_2$ = benzyl. $[CH_3NC_5H_5-C_5H_5NCH_3]^{2+}$ = N,N-dimethyl violygen.

TABLE 3

Dependence of $k_{obs}$ for $C_5H_{11}Br$ to $C_5H_{11}CN$ Conversion on Organoclay concentration$^a$

| $[Bu_3PC_{16}H_{33}]^+$-Hectorite$^b$ in Suspension, gms. | $k_{obs}$, hr$^{-1}$ |
|---|---|
| 0.025 | 0.130 |
| 0.050 | 0.303 |
| 0.075 | 0.476 |
| 0.100 | 0.575 |
| 0.125 | 0.746 |
| 0.150 | 0.891 |
| 0.175 | 1.036 |

$^a$Remaining reaction conditions: 2.0 mmole $C_5H_{11}Br$ in 6.0 ml toluene; 20.0 mmol KCN in 3.0 ml water; 90° C.
$^b$Fully exchanged, homoionic organoclay.

TABLE 4

Dependence of $k_{obs}$ for $C_5H_{11}Br$ to $C_5H_{11}CN$ Conversion on KCN Concentration$^a$

| Concentration of KCN, moles/liter | $k_{obs}$, hr$^{-1}$ |
|---|---|
| 1.67 | 0.146 |

TABLE 4-continued

Dependence of $k_{obs}$ for $C_5H_{11}Br$ to
$C_5H_{11}CN$ Conversion on KCN Concentration[a]

| Concentration of KCN, moles/liter | $k_{obs}$, hr$^{-1}$ |
|---|---|
| 3.33 | 0.278 |
| 5.00 | 0.423 |
| 6.67 | 0.575 |

[a]Remaining reaction conditions: 2.0 mmole $C_5H_{11}Br$ in 6.0 ml toluene; 3.0 ml of aqueous KCN solution; 0.10 g homoionic $[Bu_3PC_{16}H_{33}]^+$ hectorite.

TABLE 5

$k_{obs}$ Values for Conversion of Selected Alkyl Bromides to Nitriles Using Organoclays[a]

| Organoclay Catalyst | Alkyl Bromide[b] | | |
|---|---|---|---|
| | $C_5H_{11}Br$ | $C_9H_{19}Br$ | $C_{12}H_{25}Br$ |
| $MeN(C_8H_{25})_3^+$-Hectorite | 0.140 | 0.123 | 0.165 |
| $Bu_3P(C_{16}H_{33})^+$-Hectorite | 0.575 | 0.458 | 0.378 |

[a]Reaction conditions: 2.0 mmole RBr in 6 ml toluene; 20.0 mmole KCN in 3 ml water; 0.10 g homoionic organoclay; 90° C.
[b]In the formulas shown $C_5H_{11}$ = n-pentyl; $C_9H_{19}$ = n-nonyl; $C_{12}H_{25}$ = n-dodecyl.

TABLE 6

Dependence of $k_{obs}$ for $C_5H_{11}Br$ to $C_5H_{11}CN$ Conversion on Clay Host[a]

| Onium Ion | Laponite | | Hectorite | | F-Hectorite | |
|---|---|---|---|---|---|---|
| | $d_{001}$, Å | $k_{obs}$ | $d_{001}$, Å | $k_{obs}$ | $d_{001}$, Å | $k_{ob}$ |
| $[Me_3N(C_{16}H_{33})]^+$ | 14.0 | 0.011 | 18.0 | 0.164 | 28.0 | 0.12 |
| $[B_4N]^+$ | 14.0 | 0.017 | 14.7 | 0.074 | — | — |

[a]All clays were fully exchanged with the onium ion indicated and used for conversion of $C_5H_{11}Br$ to $C_5H_{11}CN$ at 90° C. under the following triphase conditions: 2.0 mmole $C_5H_{11}Br$ in 6 ml toluene; 20 mmole KCN in 3 ml $H_2O$; 0.073 meq. organoclay.

The following examples illustrate the diversity of reactions which can be catalyzed by organoclays. In addition to the cyanation reactions discussed above, it has now been found that organoclays are also useful as catalysts for the following types of organic conversions: ether synthesis, oxidation of alcohols, carbon alkylations, thiol and sulfide synthesis, dehalogenation and asymmetric synthesis.

Additional Illustrations of Organic Conversion Catalyzed by Organoclay Emulsions Example 1

Aromatic Ether Formation From Phenol Hexadecyltributyl phosphonium hectorite (0.050 mmol) was dispersed in 6ml of water containing 5.0 mmol of sodium hydroxide and 5.0 mmol of phenol and, as a separate phase, 1-bromopentane (15.0 mmol). The mixture was stirred vigorously at 90° C. to form an emulsion. After a reaction time of two hours, the emulsion was broken by centrifugation of the clay and the product, phenyl 1-pentylether, was recovered in 83.0% yield.

Example 2

Oxidation of an Alcohol to an Aldehyde

Hexadecyltributyl phosphonium hectorite (0.050 mmol) was added to a mixture containing 5 ml of 1 wt % sodium hypochlorite (NaOCl) and 3 ml of toluene containing benzyl alcohol (2.0 mmol). The mixture was stirred vigorously at 50° C. to form an emulsion. After a reaction time of 10 hr, the clay was removed by centrifugation and the benzaldehyde product was recovered from the toluene phase in 98.4% yield.

The reaction was repeated using hexadecyltributyl phosphonium fluorhectorite in place of the corresponding hectorite analog. After only 2 hr of reactions under identical conditions, the yield of benzaldehyde was 100%.

This example demonstrates that the higher charge density fluorohectorite is generally more efficient than hectorite for the formulation of an organoclay phase transfer catalyst.

Example 3

Conversion of an Alkyl Bromide to an Alkyl Thiocyanate

Hexadecyltributyl phosphonium hectorite (0.050 mmol) was added to a mixture of 4.0 ml of water containing NaSCN (10 mmol) and 1-bromopentane (5.0 mmol). The mixture was stirred vigorously to form an emulsion and after 1.5 hours reaction at 90° C., pentylthiocyanate was recovered in 95.0% yield.

The reaction was repeated using hexadecyltributyl phosphonium fluorohectorite in place of hexadecyltributyl phosphonium hectorite. After a reaction time of 3 hours, the yield of pentylthiocyanate was 100%.

Example 4

Conversion of an Alkylhalide to a Dialkylthioether

Hexadecyltributyl phosphonium hectorite (0.050 mmol) was mixed with 3.0 ml of water containing dissolved sodium sulfide (6.0 mmol) and a separate liquid phase of 1-bromopentane. The mixture was stirred vigorously to form an emulsion at 90° C. After a reaction time of 0.5 hr, the emulsion was broken by centrifugation. The 1,1-dipentylthioether product was obtained in 97.0% yield.

Example 5

Alkylation of Benzyl Cyanide

Hexadecyltributyl phosphonium hectorite (0.050 mmol) was mixed with 2.0 ml of 50 wt % of aqueous sodium hydroxide, 1-bromopentane (5.0 mmol) and benzyl cyanide 95.0 mmol). After reaction at 50° C. for 2 hr, the emulsion was broken by centrifugation and 1-cyano-1-phenyl hexane was obtained in 82.0% yield.

Example 6

Dehalogenation

Hexadecyltributyl phosphonium hectorite (0.050 mmol) was mixed with 2.0 ml of water containing dissolved sodium iodide (0.264 mmol) and sodium thiosulfate (32.0 mmol) and toluene (2.0 ml) containing dissolved 1,2-dibromo-1,2-diphenyl ethane (1.0 mml). After vigorous stirring for a reaction time of 7 hr at 90° C. the emulsion was broken by centrifugation, and 1,2-diphenylethylene was obtained in 98.0% yield.

Example 7

Reduction of Phenyl Alkyl Ketones

Phenyl alkyl ketones of the type $C_6H_5COR$, where R=n-$C_4H_9$ or t-$C_4H_9$, were reduced using $KBH_4$ at 4° C. under triphase catalysis conditions using organoclay catalysis containing chiral gallery cations:
  Cation I was the (1R,2S)(-)-N-dodecyl-N-methylephedrinium cation.
  Cation II was the (8R,9S)(-)-benzyl quininium cation.
  Table 7 summarizes the chemical and optical yields. In each reaction the volume of water was 5.0 ml and the volume of organic solvent was 3.0 ml. The optical yields were determined by polarimetry. The specific rotations for $C_6H_5CH(OH)(n-C_4H_9)$ was taken to be $[\alpha]_{d25°}=35.7(C=3,$ benzene), (J. Amer. Chem. Soc. 1981, 103 4585.) The rotation for the t-$C_4H_9$ analog was taken to be $[\alpha]_{d25°}=39.6(C=3.64,Me_2CO)$,(J. Chem. Soc. Perkin Trans.I 1978, 371.) Chemical yields were determined by gas chromotography.

Example 8

The Conversion of N-Pentyl Bromide to Cyanide

Commercial organoclays marketed by ECC International under the trade name "Claytones" are capable of emulsion formation and triphase catalyst activity.

Table 8 summarizes the time needed to achieve 73% conversion of n-pentyl bromide to the corresponding cyanide. In each case the reaction mixture contained 0.13 of organoclay, 2.0 mmol of pentyl bromide, 6.0 ml toluene, 20.0 mmol of KCN, and 3.0 ml of water. The reaction temperature was 90° C.

Included in the table for comparison purposes are the times required to achieve 73% conversion with $(C_{16}H_{33})N(CH_3)_3{}^+$ hectorite and $(C_{16}H_{33})P(n-C_4H_9)_3{}^+$-hectorite.

TABLE 7

Asymmetric Reduction of $C_6H_5COR$ Ketones at 4° C. with Chiral Organoclay Catalysts

| Cation | Clay | Ketone R-Group | KBH$_4$ mmole | Organic Solvent | Rxn time, hr. | Chem. Yield % | Optical Yield % |
|---|---|---|---|---|---|---|---|
| I | Hectorite | — | 0 | 6.0 | $C_6H_6$ | 24 | 0 | 0 |
| I | Hectorite | n-$C_4H_9$ | 5.0 | 3.0 | $C_6H_6$ | 24 | 59.0 | 7.3 |
| I | Hectorite | n-$C_4H_9$ | 5.0 | 6.0 | $C_6H_6$ | 24 | 57.2 | 7.5 |
| I | Hectorite | n-$C_4H_9$ | 2.5 | 3.0 | $C_6H_6$ | 24 | 62.7 | 6.5 |
| I | Hectorite | n-$C_4H_9$ | 2.5 | 6.0 | $C_6H_6$ | 24 | 60.0 | 6.8 |
| I | Hectorite | n-$C_4H_9$ | 2.5 | 6.0 | $C_6H_6$ | 36 | 100$^b$ | 14.4 |
| I | Hectorite | n-$C_4H_9$ | 2.5 | 6.0 | $C_6H_6$ | 36 | 100$^b$ | 13.1 |
| I | Hectorite | n-$C_4H_9$ | 2.5 | 6.0 | $C_6H_6$ | 36 | 100$^b$ | 15.0 |
| I | Hectorite | n-$C_4H_9$ | 2.5 | 6.0 | $CCl_4$ | 36 | 100 | 5.4 |
| I | Hectorite | n-$C_4H_9$ | 2.5 | 6.0 | THF | 36 | 100 | 8.6 |
| I | Hectorite | t-$C_4H_9$ | 2.5 | 6.0 | $C_6H_6$ | 24 | 100 | 0 |
| I | Hectorite | t-$C_4H_9$ | 5.0 | 3.0 | $C_6H_6$ | 24 | 100 | 0 |
| I | F-Hectorite | — | 0 | 6.0 | $C_6H_6$ | 24 | 0 | 0 |
| I | F-Hectorite | n-$C_4H_9$ | 5.0 | 3.0 | $C_6H_6$ | 24 | 100 | 0 |
| I | F-Hectorite | n-$C_4H_9$ | 2.5 | 6.0 | $C_6H_6$ | 24 | 100 | 0 |
| I | F-Hectorite | t-$C_4H_9$ | 5.0 | 3.0 | $C_6H_6$ | 8 | 100 | 10.10 |
| I | F-Hectorite | t-$C_4H_9$ | 5.0 | 6.0 | $C_6H_6$ | 8 | 100 | 10.10 |
| I | F-Hectorite | t-$C_4H_9$ | 2.5 | 3.0 | $C_6H_6$ | 8 | 100 | 10.20 |
| I | F-Hectorite | t-$C_4H_9$ | 2.5 | 6.0 | $C_6H_6$ | 8 | 100 | 10.30 |
| II | F-Hectorite | t-$C_4H_9$ | 2.5 | 6.0 | $C_6H_6$ | 8 | 100 | 14.5 |
| II | F-Hectorite | t-$C_4H_9$ | 2.5 | 3.0 | $C_6H_6$ | 8 | 100 | 15.3 |
| II | F-Hectorite | t-$C_4H_9$ | 5.0 | 6.0 | $C_6H_6$ | 8 | 100 | 20.3 |
| II | F-Hectorite | t-$C_4H_9$ | 5.0 | 3.0 | $C_6H_6$ | 8 | 100 | 20.2 |
| II | F-Hectorite | t-$C_4H_9$ | 5.0 | 6.0 | $C_6H_6$ | 8 | 100$^b$ | 23.9 |
| II | F-Hectorite | t-$C_4H_9$ | 5.0 | 6.0 | $C_6H_6$ | 8 | 100$^b$ | 26.5 |

$^a$Reaction conditions are provided in the text.
$^b$In these experiments the ketone was added slowly to the reaction mixture over a period of 3-14 hr.

TABLE 8

Reaction Times Required for 73% Conversion of n-Pentyl Bromide to n-Pentyl Cyanide$^a$

| Clay | Time, hr. |
|---|---|
| ECC CLAYTONE T-40 | 8 |
| ECC CLAYTONE T-AF | 8 |
| ECC CLAYTONE F-PS | 8 |
| $(C_{16}H_{33})N(CH_3)_3{}^+$-Hectorite | 4.6 |
| $(C_{16}H_{33})P(n-C_4H_9)_3{}^+$-Hectorite | 1.5 |

$^a$Reaction conditions given in Example 8

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

We claim:

1. A method of carrying out an organic substitution reaction between a nucleophile dissolved in an aqueous liquid phase and an electrophile dissolved in an immiscible organic liquid phase by contacting under agitation the two liquid phases with an onium ion exchange form of a 2:1 layered silicate clay catalyst to form a triphase emulsion wherein the clay-bound onium ion is a quaternary ammonium, phosphonium or arsonium ion of the type $[R_{4-x}AR'_x]^+$, where A=N, P, or As; the R moieties are large organo groups consisting of an alkyl group of five or more carbon atoms when x=1, 2, or 3 and four or more carbon atoms when x=0, and R' are small organo groups selected from one or more members of the group methyl, ethyl, propyl, butyl, ethoxyl, propoxyl, phenyl or benzyl.

2. A method according to claim 1, in which the clay-bound onium ion is (1R, 2S)(-)-N-dodecyl-N-methylephedrinium.

3. A method according to claim 1, in which the clay-bound onium ion is (8R,9S)(-)-benzyl-quininium.

4. A method according to claim 2 in which the onium ion is a N-alkylpyridinium ion wherein the alkyl group contains five or more carbon atoms.

5. The method according to claim 1 in which the quaternary onium ion is (n-$C_{14}H_{39}$)NMe$_3{}^+$, (n-$C_{16}H_{33}$)NMe$_3{}^+$, (n-$C_{14}H_{29}$)NMe$_2$(CH$_2$C$_6$H$_5$)$^+$, (n-$C_{16}H_{33}$)NMe$_2$(CH$_2$C$_6$H$_5$)$^+$, (n-$C_{18}H_{37}$)NMe$_2$(CH$_2$C$_6$H$_5$)$^+$, (n-$C_{12}H_{25}$)$_2$NMe$_2{}^+$, (n-$C_8H_{17}$)$_3$NMe$^+$, where in Me is methyl, and (n-$C_4H_9$)$_4$N$^+$.

6. A method according to claim 1, in which the charge density of the 2:1 layered silicate is greater than 0.4 electrons per $O_{20}(OH)_4$, $O_{20}(OH,F)_4$ or $O_{20}F_4$ unit.

7. The method according to claim 1, in which the silicate is a smectite clay and has a charge density in the range of 0.6 to 1.2 charge units per $O_{20}(OH)_4$, $O_{20}(OH,F)_4$ or $O_{20}F_4$ unit.

8. The method according to claim 1, in which the catalyst is an essentially completely cation exchanged, homoionic clay.

9. The method according to claim 1, in which at least about 25% of the inorganic exchange ions of the clay are replaced by organic onium ions.

10. The method according to claim 1, in which the emulsion is broken by centrifuging or by filtering to recover the products.

* * * * *